(12) United States Patent
Dearden et al.

(10) Patent No.: US 10,639,480 B2
(45) Date of Patent: May 5, 2020

(54) NEUROSTIMULATORS AND STIMULATION SYSTEMS

(71) Applicant: THE ALFRED E. MANN FOUNDATION FOR SCIENTIFIC RESEARCH, Santa Clarita, CA (US)

(72) Inventors: Brian R. Dearden, Pasadena, CA (US); Harshit Suri, Pasadena, CA (US); Edward K. F. Lee, Fullerton, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 169 days.

(21) Appl. No.: 15/851,646

(22) Filed: Dec. 21, 2017

(65) Prior Publication Data
US 2018/0178015 A1 Jun. 28, 2018

Related U.S. Application Data

(60) Provisional application No. 62/438,023, filed on Dec. 22, 2016.

(51) Int. Cl.
*A61N 1/36* (2006.01)
*A61N 1/02* (2006.01)
*A61N 1/05* (2006.01)
*A61N 1/372* (2006.01)

(52) U.S. Cl.
CPC ......... *A61N 1/36196* (2013.01); *A61N 1/025* (2013.01); *A61N 1/0504* (2013.01); *A61N 1/0534* (2013.01); *A61N 1/36171* (2013.01); *A61N 1/37223* (2013.01); *A61N 1/37235* (2013.01); *A61N 1/0553* (2013.01); *A61N 1/0556* (2013.01); *A61N 1/36067* (2013.01); *A61N 1/36075* (2013.01); *A61N 1/36178* (2013.01)

(58) Field of Classification Search
CPC ............................ A61N 1/36196; A61N 1/025
USPC ............................................................ 607/46
See application file for complete search history.

(56) References Cited

U.S. PATENT DOCUMENTS

| | | | |
|---|---|---|---|
| 6,735,475 B1 | 5/2004 | Whitehurst |
| 7,684,873 B2 | 3/2010 | Gerber |
| 7,853,321 B2 | 12/2010 | Jaax |
| 8,280,515 B2 | 10/2012 | Greenspan |
| 8,666,498 B2 | 3/2014 | Newman |

(Continued)

FOREIGN PATENT DOCUMENTS

WO 2016/049041 A1 3/2016

OTHER PUBLICATIONS

International Search Report, dated Apr. 16, 2018, International Patent Application No. PCT/US2017/068043.

(Continued)

*Primary Examiner* — Nadia A Mahmood
(74) *Attorney, Agent, or Firm* — Philip Lee

(57) ABSTRACT

In accordance with the present invention, various embodiments of neurostimulators and stimulation systems are disclosed that provide different shapes and patterns of stimulus pulses and trains of pulses with fixed and no fixed frequencies. The neurostimulator can be configured to provide high frequency stimulation and also be implantable in the head or neck regions in order to stimulate nerves and nerve ganglions in the head and neck regions and also stimulate the brain.

25 Claims, 5 Drawing Sheets

(56) References Cited

U.S. PATENT DOCUMENTS

| | | | |
|---|---|---|---|
| 8,731,676 B2 | 5/2014 | Fang | |
| 8,843,202 B2 | 9/2014 | Greenspan | |
| 8,983,612 B2 | 3/2015 | Fang | |
| 9,042,991 B2 | 5/2015 | Reed | |
| 9,295,839 B2 | 3/2016 | Thacker | |
| 9,295,841 B2 | 3/2016 | Fang | |
| 2002/0161403 A1 | 10/2002 | Meadows | |
| 2006/0004423 A1* | 1/2006 | Boveja | A61N 1/08 607/46 |
| 2013/0218239 A1* | 8/2013 | Grill | A61N 1/36189 607/72 |
| 2014/0243924 A1* | 8/2014 | Zhu | A61N 1/36146 607/46 |
| 2016/0158540 A1 | 6/2016 | Mouchawar | |

OTHER PUBLICATIONS

Written Opinion, dated Apr. 16, 2018, International Patent Application No. PCT/US2017/068043.

\* cited by examiner

NEUROSTIMULATORS AND STIMULATION SYSTEMS

CROSS REFERENCE TO RELATED APPLICATION

This application claims the benefit of U.S. Provisional Application No. 62/438,023, filed Dec. 22, 2016.

FIELD OF THE INVENTION

The present invention relates to implantable neurostimulators, electrode leads, stimulation systems and methods of use and, more particularly, relates to stimulation of nerve targets in the head (including facial and chin) and neck areas to treat various ailments, including headache, migraine, and facial pain. In addition, the present invention relates to implantable neurostimulators and systems for use in deep brain stimulation to treat such conditions as Parkinson's disease and essential tremor.

BACKGROUND OF THE INVENTION

Most neurostimulators on the market were originally developed for stimulation of nerves in the spinal cord to treat chronic pain. In most cases the neurostimulators were not intended for stimulation of nerves in the neck and face. The neurostimulators can be relatively large, since they were designed to be placed in the body such as the torso and chest areas. Because of their relatively large size, when these neurostimulators have been adapted for use (off-label) by physicians to stimulate nerves in the neck or head area, they have been implanted in the chest, torso, or back of the patient and not in the head.

In addition, the typical neurostimulators that have been available deliver electrical stimulation that is a train of pulses with selected, fixed parameters such as pulsewidths, amplitudes, and stimulus frequency. Stimulus pulse amplitudes are generally a constant voltage or a constant current amplitude, but not both. Whether the neurostimulator provides constant voltage stimulus or constant current stimulus is based on the design of the neurostimulator. These typical stimulation choices are limiting and are not optimal for every treatment use.

Headache, migraine, and facial pain disorders are a substantial health concern that can have a negative impact on social activities and work. In some instances, it can lead to over consumption of pain relieving drugs. There has been some clinical work to use neurostimulators that have been designed for spinal cord stimulation to treat headache and migraine. The neurostimulator is implanted subcutaneously (under the skin) either in the chest or back area of a patient and a stimulation lead or leads, connected to the neurostimulator, are tunneled underneath the skin, up the neck, and to a target nerve such as the occipital nerve. Stimulation (usually a train of electrical stimulus pulses at a fixed frequency) is delivered from the neurostimulator and via electrode contacts located at the distal end of the stimulation lead or leads to stimulate the target occipital nerve in order to alleviate migraine or headache.

There are some drawbacks with these existing adapted neurostimulator systems. The spinal cord neurostimulators are relatively bulky and were never intended to be implanted in the head, so they must be implanted in the back, torso or chest of a patient. The leads must be tunneled through the neck into the head. Since there is a great deal of movement in the neck, there will be twisting action that causes the stimulation lead to move. It is desirable to minimize lead movement once the lead is implanted.

In addition, it has been found that the conventional, fixed stimulation frequencies, e.g., 35 Hz, offered by these neurostimulators, while adequate for conventional spinal cord stimulation, do not always provide relief from migraines or headaches. Unlike the mechanism of chronic pain that is treated with spinal cord stimulation, headaches and migraines are believed to arise from many different causes and, hence, the present inventors have surmised that a neurostimulator that can offer a wider variety of stimulation other than a fixed 35 Hz stimulation would have a greater chance to successfully treat more incidences of headaches and migraines.

Neurostimulators and stimulation leads used in spinal cord stimulation have also been adapted for use in deep brain stimulation ("DBS"). Deep brain stimulation is currently being used to treat movement disorders such as Parkinson's disease and essential tremor. A lead extension may be used to connect the neurostimulator to the stimulation lead. The lead extension or the stimulation lead is tunneled subcutaneously through the neck and to the top of the head, through a hole at the top of the skull, and into the brain. Again, the drawbacks are that the neurostimulator has to be placed in the chest, torso or back and not in the head. The stimulation lead or lead extension must be tunneled through the neck which subjects the lead or lead extension to unwanted movement.

Nevro Corporation provides a neurostimulator in their HF10™ system that is approved and marketed purely for spinal cord stimulation and which offers selectable stimulus frequencies up to 10 kHz. Stimulus amplitudes and pulsewidths, as well as frequencies appear to be fixed, once selected and programmed. The Nevro neurostimulator is sized and shaped to be placed generally in the torso back, side or front chest area, and is specifically designed to stimulate the spinal cord with multiple stimulation channels. The Nevro neurostimulator is not intended to be implanted in the head since it is too large and bulky. Although the Nevro neurostimulator offers higher frequency stimulation than conventional spinal cord stimulators, the Nevro device cannot be implanted in the head. In addition, there is no known use of a Nevro neurostimulator for stimulating nerves in the head or neck or stimulating the brain for DBS application.

It would be desirable to have neurostimulators and stimulation systems that can provide a wider choice of stimulation patterns to stimulate various nerves in the body, and in particular nerves and ganglions in the head, face and neck and also for DBS applications.

SUMMARY OF THE INVENTION

The present invention address the above and other needs by providing a neurostimulator and stimulation systems that can be implanted in the head to stimulate nerves and nerve ganglions in the head and neck and also to stimulate the brain. As referred to herein in this disclosure, the word "head" will be used inclusively to include the face, chin, under the chin, as well as the back, top and sides of the head. Embodiments of the inventive neurostimulator and stimulation system can be used for deep brain stimulation.

In one embodiment, in accordance with the invention, a stimulation system is provided comprising: an implantable neurostimulator having a housing that is sized and shaped to be implanted subcutaneously in the head area; and at least one lead connected to the neurostimulator, the lead having one or more electrode contacts, wherein the neurostimulator is configured to provide a train of stimulus pulses having a frequency in the range covering at least 20 Hz to 4.8 kHz.

In another embodiment, in accordance with the invention, an implantable stimulation system is provided comprising: a neurostimulator having a housing that is sized and shaped to be implanted in the head or neck; and at least one stimulation lead that can be connected to the neurostimulator, the lead having one or more electrode contacts, wherein the neurostimulator is capable of providing a selectable stimulus frequency in at least the range from about 100 Hz to about 4.8 kHz.

The neurostimulator can be capable of providing a selectable stimulus frequency in at least the range from about 500 Hz to about 4.8 kHz. For clarity of meaning as used in this disclosure, a neurostimulator having a programmable frequency range of 50 Hz to 5.0 kHz would meet the frequency range requirement "in at least the range from about 500 Hz to about 4.8 kHz," since the latter range is entirely covered by the first stated range. In other embodiments, a neurostimulator can be capable of providing a selectable stimulus frequency in at least the range from about 500 Hz to about 4.8 kHz; in at least the range of about 100 Hz to about 4.8 kHz; and in other embodiments, in at least the range of about 100 Hz to about 500 Hz. In all the above embodiments mentioned, the stimulation lead may be configured to stimulate, among other nerves in the head and neck, the occipital nerve, its branches, the trigeminal nerve or its branches. In all the above embodiments, the stimulation leads may have at the distal ends paddle-type electrode leads, cuff-type electrode leads or linear-type (percutaneous) electrode leads.

The implantable stimulation system can also include external (not implanted) system components such as a patient programmer and/or a clinician programmer which can be used to communicate, program, and query the implanted neurostimulator.

In another embodiment, in accordance with the invention, a neurostimulator is provided comprising: at least one lead connector for connecting at least one stimulation lead having one or more electrode contacts, wherein the neurostimulator is configured and capable of providing stimulation with a pulse electrical stimulus frequency at least in the range of about 20 Hz to 4.8 kHz. In some embodiments, the neurostimulator has a housing that is sized and shaped to be implanted subcutaneously over the skull.

In another embodiment, in accordance with the invention, a neurostimulator is provided comprising: a housing that is sized and shaped to be implanted subcutaneously over the skull; and at least one lead connector for connecting at least one stimulation lead having one or more electrode contacts, wherein the neurostimulator is capable of providing stimulation with a pulse electrical stimulus frequency in at least the range from about 100 Hz to about 4.8 kHz. In some embodiments, a neurostimulator can be capable of providing a selectable stimulus frequency in at least the range from about 500 Hz to about 4.8 kHz; in at least the range of about 100 Hz to about 4.8 kHz; and in at least the range of about 100 Hz to about 500 Hz.

In another embodiment, in accordance with the invention, a neurostimulator is provided comprising: an electrical circuit capable of delivering a train of electrical stimuli that has at least a train of n number of pulses in one polarity and followed by a train of at least m number of pulses in the opposite polarity, where n and m are both equal to 2 or greater whole numbers.

In some embodiments, n and m are equal whole numbers and the sum of n pulses is charge-balanced with the sum of m pulses. In some embodiments n pulses and m pulses have a current amplitude or voltage amplitude which are substantially different. In some embodiments n and m are unequal whole numbers and the sum of charges provided by n pulses is substantially charge-balanced with the sum of charges provided by m pulses. In some embodiments the neurostimulator can be shaped and sized for implantation in the head or neck subcutaneously. In some embodiments, the neurostimulator can be shaped and sized for implantation in the chest region or pectoral region of the body.

In another embodiment, in accordance with the invention, an implantable neurostimulator comprises: an electrical circuit capable of delivering, through at least one electrode contact, a train of electrical stimuli that has at least n number of stimuli, where n is 3 or a greater whole number, such that each stimulus is represented by N1, N2, . . . , N-Last in one time window and where the train of stimuli does not have a fixed frequency.

In some embodiments, the frequency is not fixed but is variable as measured between the time duration between N1 and N2 compared to the time duration N2 and N3. In some embodiments, the duration between adjacent stimuli is entirely randomized with no fixed frequency, where the total number of stimuli represented by N1, N2, . . . , N-Last, occurring in a time window can be selectable through software programming that is resident in the neurostimulator. In some embodiments, the neurostimulator can be sized and shaped to be implanted in the head or neck subcutaneously. In other embodiments, the housing is comprised of a conductive metal capable of being selected and used as an indifferent return electrode to operate in a monopolar stimulation mode.

In some embodiments, each stimuli N1, N2, . . . , N-Last, is biphasic, having a peak in both polarity directions and is charge balanced. In other embodiments, each stimuli N1, N2, . . . , N-Last, can be symmetric and charge balanced. In some embodiments, each stimuli N1, N2, . . . , N-Last, can be biphasic, not symmetric, and charge balanced.

In a further embodiment, in accordance with the invention, a stimulation system comprises: an implantable neurostimulator and at least one lead connected to the neurostimulator, the lead having one or more electrode contacts and configured to be implanted in the brain, where the neurostimulator is capable of providing a train of stimulation pulses having a frequency from about 20 Hz to about 50 KHz. The neurostimulator may be shaped and sized to be implanted subcutaneously in the head.

In yet a further embodiment, in accordance with the invention, a deep brain stimulation system comprises: an implantable neurostimulator; and at least one lead that can be connected to the neurostimulator, the lead having one or more electrode contacts and configured to be implanted in the brain, where the neurostimulator is capable of providing a selectable stimulus frequency in at least the range from about 100 Hz to about 4.8 KHz. In some embodiments, a neurostimulator can be capable of providing a selectable stimulus frequency in at least the range from about 500 Hz to about 4.8 kHz; in at least the range of about 100 Hz to about 4.8 kHz; and in at least the range of about 100 Hz to about 500 Hz.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is the best mode for presently contemplated for carrying out the invention. This description is not to be taken in a limiting sense, but is made merely for the purpose of describing the general principles of the invention. The scope of the invention should be determined with reference to the claims.

Figure 1:
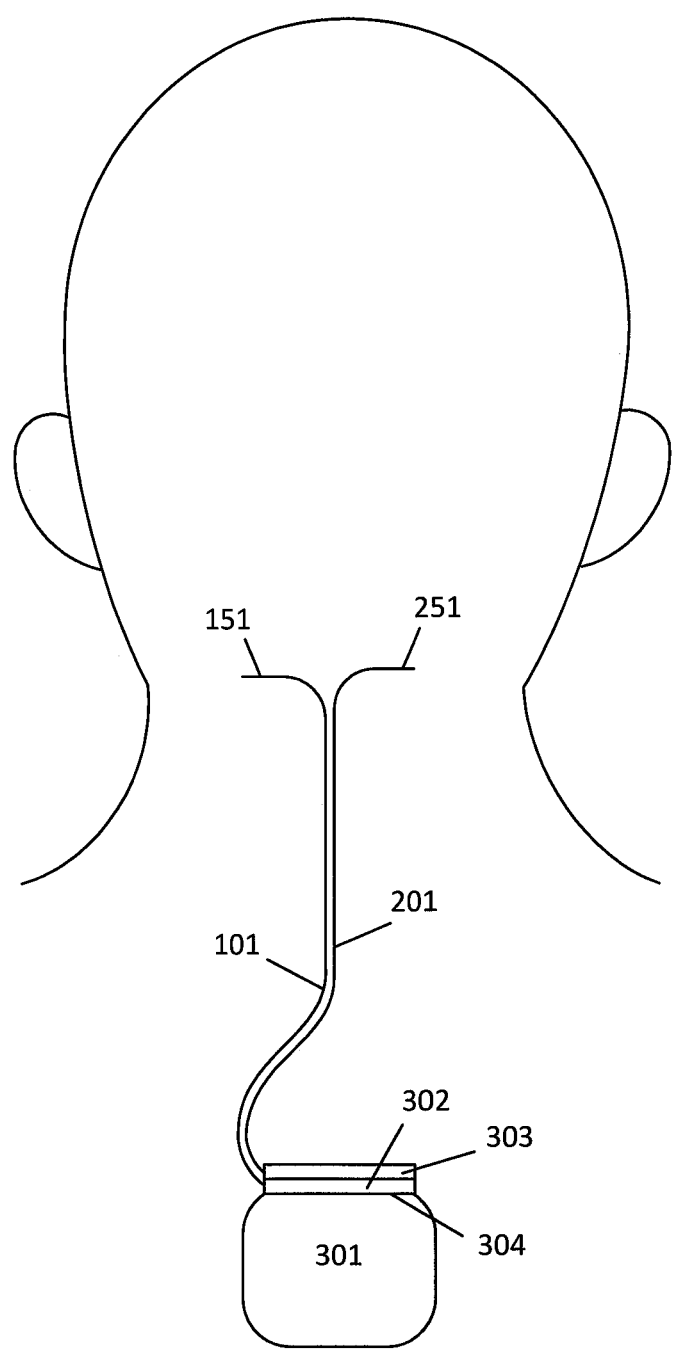
FIG. 1 shows, in accordance with the present invention, an illustration of a neurostimulator and lead, where the neurostimulator is implanted in the back.
Figure 2:
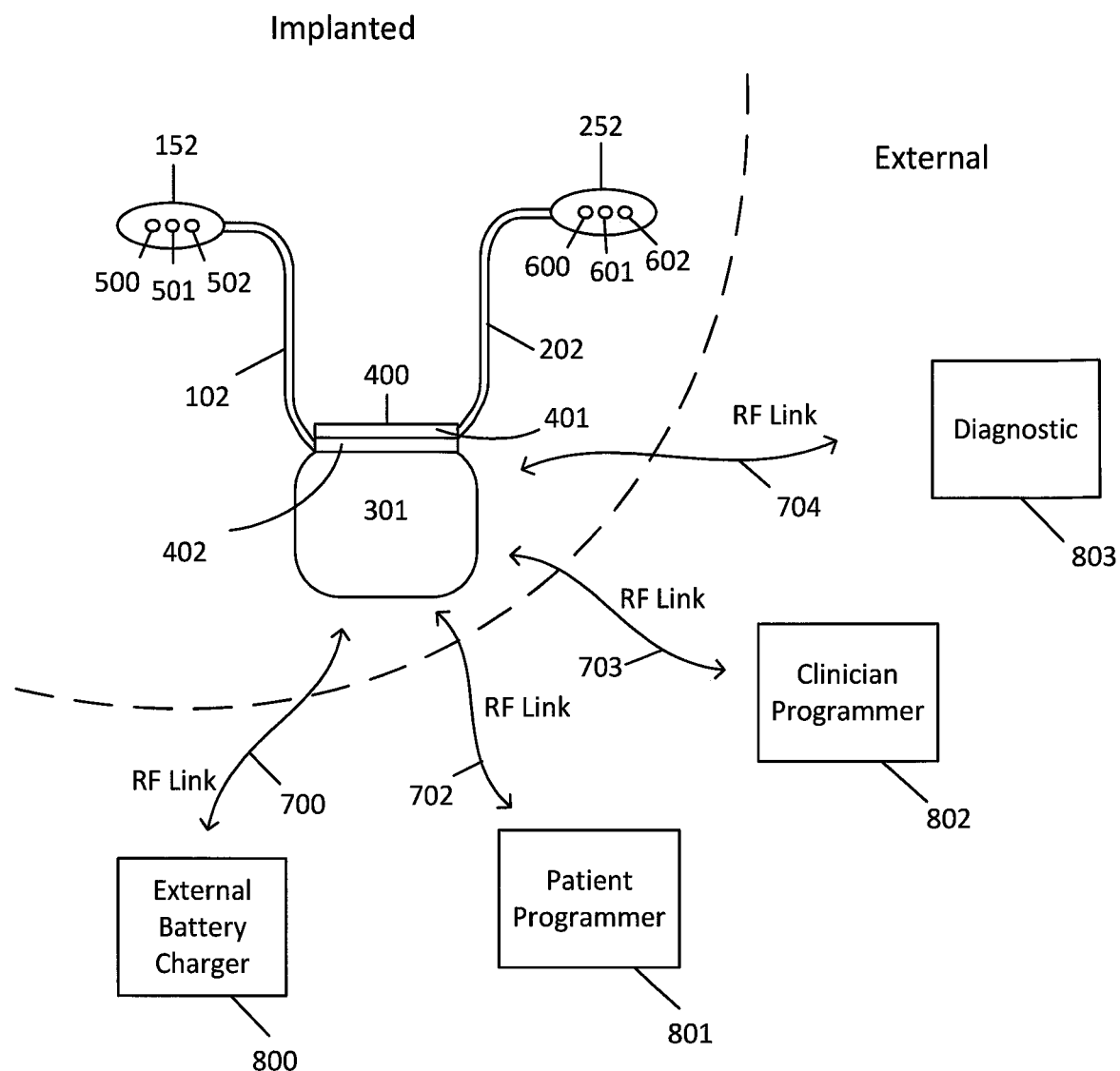
FIG. 2 shows, in accordance with the present invention, an illustration of a total stimulation system showing the neurostimulator and lead system that is implanted in the body with ancillary external devices.

FIG. 1 shows, in accordance with the present invention, an embodiment of a stimulation system with a neurostimulator 301 having a connector block 302 with two lead connectors 303 and 304 for connecting two leads 101 and 201, respectively. The leads have at their distal ends a set of electrode contacts 151 and 251 made from conductive metal such as a platinum-iridium which are typical implantable electrode contact materials. An example of a linear or percutaneous electrode lead is shown in the following: U.S. Pat. No. 6,510,347. Another choice of leads is the kind having paddle electrodes 152 and 252 (shown in FIG. 2) at the distal portion of the leads, the electrodes having one or more electrode contacts 500, 501, 502 and 600, 601, and 602, as shown in FIG. 2. An example of a paddle-type electrode lead is shown in U.S. Pat. No. 7,697,995. The neurostimulator can be implanted in the upper chest area below the clavicle, by wrapping the leads 102 and 202 around the neck.

FIG. 2 shows, in accordance with the present invention, an embodiment of a stimulation system which includes a neurostimulator 301 with a pair of leads 102 and 202. When the length of leads 102 or 202 is too short and needs to be longer, a lead extension (not shown) may be used to connect the lead 102 to the neurostimulator 300 and/or lead 202 to the neurostimulator. The stimulation system can include a diagnostic programmer 803 so that the manufacturer can communicate via an RF link 704 with the neurostimulator before and after its implantation for the purpose of testing and gathering data from the neurostimulator 301.

The clinician programmer 802 may be used by the clinician or care-giver to program the neurostimulator 301 with an RF link 703 and also receive patient and device data from the neurostimulator which may be used for diagnostic purposes. Examples of parameters which may be programmed are basic stimulus parameters such as voltage or current amplitudes, stimulus pulsewidths and frequencies of a train of stimuli. The patient programmer 801 can be a hand-held programmer that the patient can operate to make limited programming choices with an RF link 702 to adjust parameters such as stimulus voltage or current amplitudes and frequencies in order to fine tune parameter settings.

An external battery charger 800 may be included in the stimulation system if the neurostimulator 301 does not use a primary, one-time-use only battery, but instead the neurostimulator contains a rechargeable battery that may be recharged transcutaneously using inductive coupling. The external charger itself may contain at least a first coil that is used for inductive coupling with the neurostimulator 301 to transfer power through the coil in the external charger to a receiving coil inside the neurostimulator 301. The first coil may be external to the battery charger housing, connected to the battery charger by a cord. A separate, second coil may be inside the battery charger housing or the second coil may be external and also connected by a cord to the battery charger housing, which second coil is used for communication with the implanted neurostimulator 301. If the neurostimulator contains and uses a primary, one-time-use only battery, the battery charger 800 would not be needed in such a stimulation system. Communication between the external battery charger 800 and neurostimulator 301 can occur via an RF link 700.

Figure 3:
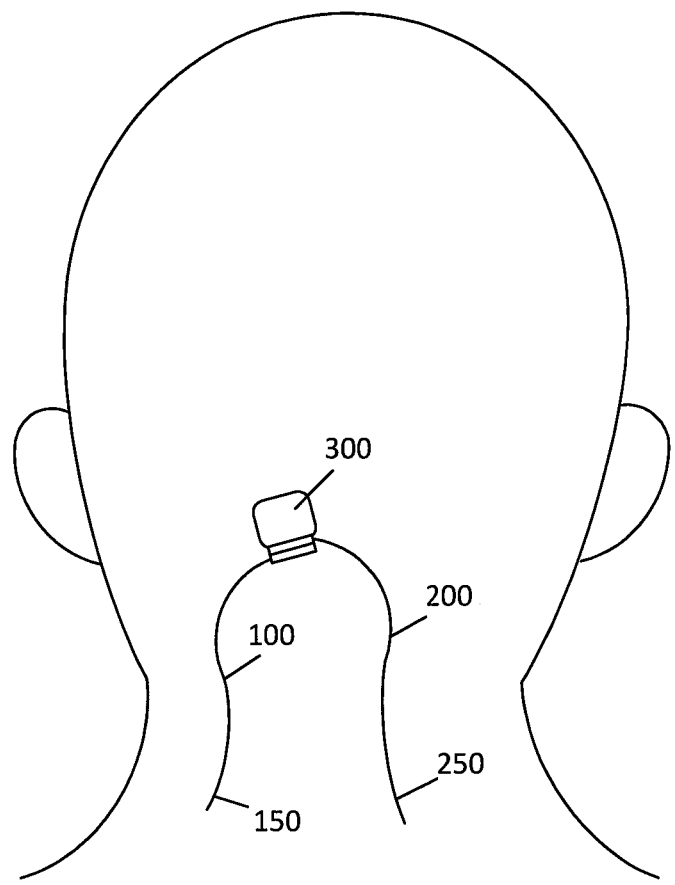
FIG. 3 shows, in accordance with the present invention, an illustration of a neurostimulator that can be implanted in the head.

FIG. 3 shows, in accordance with the present invention, a neurostimulator 300 and lead 100, 200 system with electrodes 150, 250, where the neurostimulator 300 is sized and shaped to be implanted over the surface of the skull and underneath the skin, i.e., subcutaneously. Such a neurostimulator 300 may have a smaller housing than a neurostimulator 301, which is sized and shaped to be implanted in a body area other than the neck and head. Neurostimulator 300 must necessarily be smaller in volume than neurostimulator 301 and be shaped so as to not protrude out while implanted in the head. Because of practical implant limits on the largest size of the neurostimulator 300 that can be implanted in the head, if a primary battery is used in the neurostimulator, it must be relatively small in volume and yet, last for many years. Using a rechargeable battery in neurostimulator 300 will permit using a smaller housing and obviate the need to have more frequent replacements of the neurostimulator which has a primary, one-time-use only, battery. Neurostimulator 300 may be shaped to accommodate the surface curvature of the human skull.

The neurostimulator 300 or 301 is depicted in FIGS. 1, 2, and 3 as having two lead connectors, connected to two leads, but in some embodiments in accordance with the present invention, there will only be a single lead connector, or in other embodiments in accordance with the invention, three, four or even more lead connectors may be present in the neurostimulator. In some embodiments, the neurostimulator 300, 301 can be integrally connected to one or more leads with no lead connector, i.e., the leads or leads are permanently connected to the neurostimulator and cannot be disconnected. In addition, in some embodiments, the neurostimulator 300 or 301 can have a housing made at least partially from a conductive metal that can be selectably activated (programmed on) so that the conductive metal functions as an indifferent or return electrode to provide a monopolar or unipolar electrical stimulation circuit via at least one electrode contact on at least one lead. As used herein, a "monopolar stimulation" or "unipolar stimulation" uses the neurostimulator housing conductive metal as one electrode contact, which will be referred to as an "indifferent electrode" or a "return electrode" and also uses at least one of the electrode contacts from at least one lead, as part of the complete stimulation circuit. It is possible to have monopolar stimulation occur using two or more electrode contacts, simultaneously, but the housing must also be functioning simultaneously as the return or indifferent electrode.

The neurostimulator 300, 301 may also be optionally operated (programmed to ON in software) in a bipolar mode where the housing is not part of the stimulation circuit and at least two electrode contacts in a single stimulation lead or at least two separate electrode contacts located on a plurality of leads must be used to provide a complete bipolar stimulation circuit. A "bipolar" stimulation will be defined herein as having a stimulation circuit that utilizes at least two electrode contacts, where at any single point in time or simultaneously, at least one electrode contact in the circuit is functioning as a cathode and at least one electrode contact in the circuit is functioning as an anode. Generally, each electrode contact in the stimulation circuit will function alternatively, in time, as both an anode and cathode. In fact, ideally, each electrode contact will generally put out current and draw in current in the same quantity of charges within some narrow time window so as to prevent degradation of the electrode contact over a long period of time. This equality in the quantity of charges going in and out of a single electrode contact is call "charge-balancing". If an electrode contact is operating more of the time as a cathode or more of the time as an anode in a time window, that charge imbalance will eventually cause the electrode contact to degrade over time. It is generally desirable to achieve stimulation charge balancing so that the electrode contact or contacts will last for many years while implanted the body.

FIGS. 4A-4D show, in accordance with the present invention, embodiments of stimulation regimes and stimuli that can be delivered by the neurostimulators in the present invention.

Figure 4A:
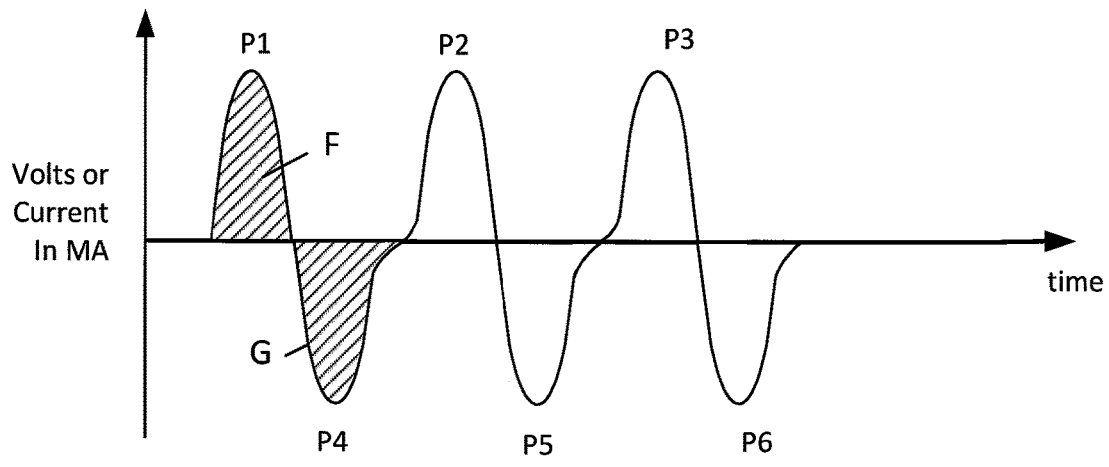
FIGS. 4A-4D show, in accordance with the present invention, example stimulus shapes and patterns that the neurostimulator depicted in FIGS. 1, 2, and 3 can deliver via the electrode contact or contacts on the lead.

FIG. 4A shows, in accordance with the present invention, a train of stimuli. The drawing shows, by way of example only, three stimuli in succession in the train, although the train can be any number of stimuli in succession as desired. For the sake of clarity, the train of stimuli depicted shows the output current or voltage amplitude at one electrode contact over time. Each stimulus has two phases. If the upward direction depicted as peaks P1, P2 or P3, is assigned as representing cathodic current into the tissue from the chosen electrode contact, then the downward direction depicted by peaks P4, P5 and P6 would represent the same electrode contact functioning as an anode. The areas within the peaks, representing total charge, depicted as F and G, are the same and therefore the single stimuli represented by peaks P1 and P4 would represent a charge-balanced, bi-phasic pulse having symmetry. In the present invention, the neurostimulator 300, 301, is configured in one embodiment to be programmable to deliver a full range of stimulus frequencies of between about 10 Hz to about 40 kHz, in some predetermined frequency increments. Other embodiments of neurostimulators will deliver stimulus range of frequencies at least between about 500 Hz to 4.8 kHz. Still other embodiments of neurostimulators will at least deliver stimulus frequency ranges from about 500 Hz to about 2 kHz. The neurostimulator 300, 301 of the present invention can operate in either monopolar or bipolar modes, by choice.

Figure 4B:
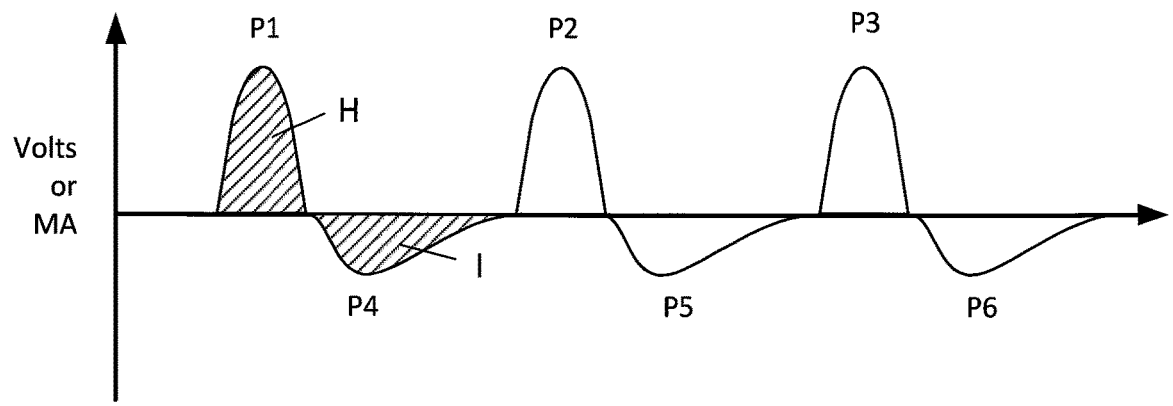

FIG. 4B shows, for the neurostimulator of the present invention, another possible embodiment of stimulation train of stimuli. Each stimulus having peaks P1 and P4, is not symmetric because the amplitudes, whether in volts or current (mA), are not equal. However, the areas under the curve, H and I, representing total charges are equal, and so the stimulus is charge balanced. In the present invention, in one embodiment, the neurostimulator 300, 301, can be configured to be programmable to deliver a full range of stimulus frequencies of between about 10 Hz to about 40 kHz. Some other frequency ranges that can be used include coverage of frequencies at least between about 500 Hz to about 4.8 kHz. Another frequency range that can be used includes or covers at least from about 500 Hz to about 2.0 kHz. The neurostimulator can function in either monopolar or bipolar modes, by choice.

Figure 4C:
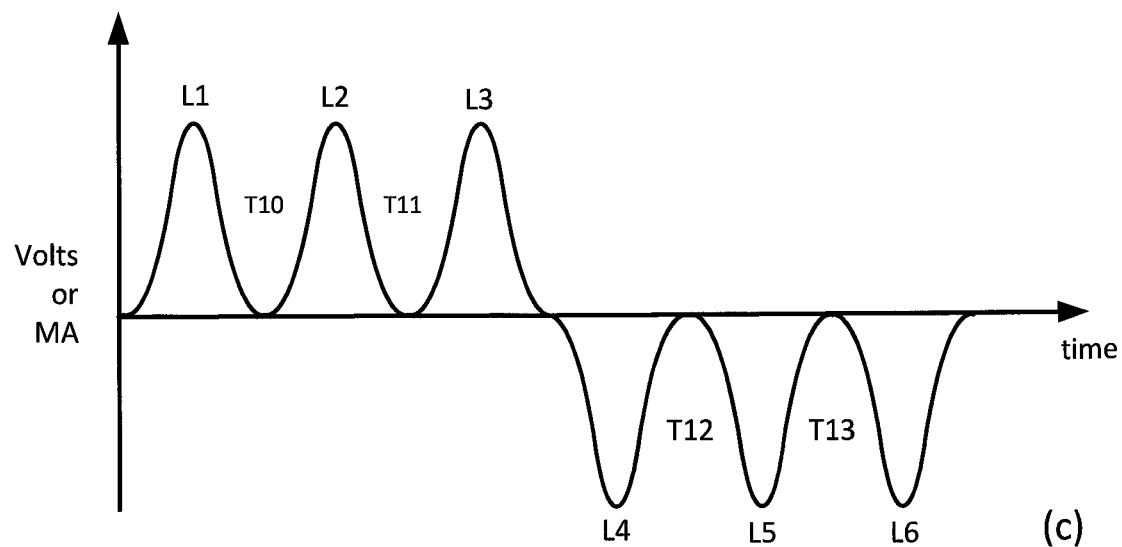

FIG. 4C shows another possible embodiment of a stimulation train of stimuli, from an embodiment of the neurostimulator. The stimulus having peak amplitude (volts or mA) L1 is not biphasic. Stimuli having peak amplitudes (volts or mA) L2 and L3 are also not biphasic. However, considered together as a train of stimuli having amplitudes L1, L2, L3 and L4, L5 and L6, they will be charge-balanced when viewed from electrical charge exiting and returning in a single electrode contact over some brief time window. In some embodiments, the duration of time between adjacent pulses, e.g, T10 and T11 may be different, so that there is no fixed frequency. Similarly, T12 and T13 may not be equal and may also be different from T10 and T11. The times T10, T11, T12, T13 may be different and determined in advance through selected software programming using the clinician programmer or, in some cases, the patient programmer. Or the times T10, T11, T12, T13 may be different because they are randomized but within a certain programmed maximum time duration between two adjacent pulses. In this case, the frequency of stimulation is not fixed, but variable. The neurostimulator can be selected to function in either monopolar or bipolar stimulation modes.

Figure 4D:
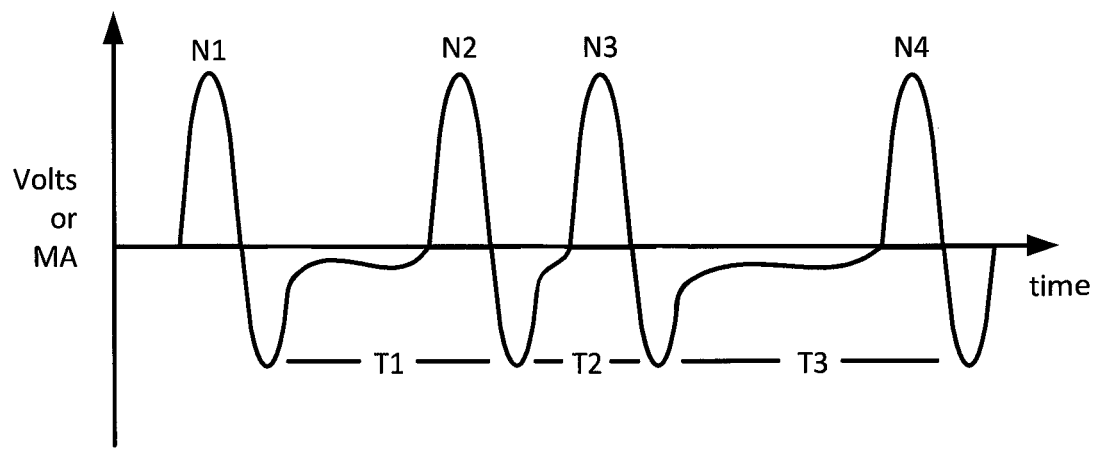

FIG. 4D shows more embodiments of a train of stimuli in accordance with the present invention. Here, a train of stimuli, represented as N1, N2, N3 and N4 . . . and so on until N Last, can have equal peak amplitudes. However, the time duration between adjacent stimuli, T1, T2, T3, T4 . . . T-Last, may all be different, either programmed in advanced to all be different or randomly generated, but where T1, T2, T3, T4 . . . T-Last cannot exceed some predetermined maximum time duration. Each stimulus is biphasic and charge balanced. There is no true fixed frequency. The neurostimulator can be selected to operate in either monopolar or bipolar modes.

In one embodiment, a stimulation system comprises: an implantable neurostimulator having a housing that is (a) sized and shaped to be implanted subcutaneously in the head or neck area and (b) where the neurostimulator is configured to provide a train of stimulus pulses having a frequency at least in the range covering about 20 Hz to 4.8 kHz. The frequency range offered by the neurostimulator can be a narrower range, for example, from about 100 Hz to about 4.8 kHz in order to have a neurostimulator that is less challenging to make. Other possible ranges are about 500 Hz to about 4.8 kHz. For clarity of meaning as used in this disclosure, a neurostimulator having a programmable frequency range of 250 Hz to 5.0 kHz would meet the frequency range requirement "from 500 Hz to 4.8 kHz" because the latter frequency range which is narrower is covered entirely by the former frequency range, which is wider. In other embodiments the neurostimulator may have a stimulus frequency at least in the range of about 100 Hz to about 4.8 kHz and yet another embodiment, at least in the range of about 100 Hz to about 500 Hz. All of these embodiments of stimulation frequency ranges, in accordance with the present invention, will provide a wider stimulus frequency choice than a conventional spinal cord neurostimulator that generally uses low stimulation frequencies such as 35 Hz.

In all the above embodiments mentioned, the stimulation lead may be configured to stimulate, among other nerves in the head and neck, the occipital nerve or its branches or the trigeminal nerve or its branches. The stimulation leads may have at the distal ends paddle-type electrode leads, cuff-type electrode leads or linear-type (percutaneous) electrode leads. Examples of cuff-type lead electrodes are found in Patent Numbers: U.S. Pat. Nos. 3,774,618, 3,654,933 and 9,227,053.

The implantable stimulation system can also include external (not implanted) system components such as a patient programmer 801 and/or a clinician programmer 802 which can be used to communicate, program and query the implanted neurostimulator 300, 301.

In some embodiments, the neurostimulator has a housing that is sized and shaped to be implanted subcutaneously over the skull. The shape of the neurostimulator housing should be much flatter and smaller than a conventional spinal cord neurostimulator. This will permit the neurostimulator to be implanted over the skull and beneath the scalp. Generally, in order to keep the neurostimulator size small enough to implant in the head or neck area, the battery is preferably a rechargeable battery that can be charged inductively through the skin. A primary, one-time-use only battery could be used as battery technology improves over time by decreasing battery size, while increasing longevity.

In some embodiments, a neurostimulator is provided comprising: an electrical circuit capable of delivering a train of electrical stimuli that has at least a train of n number of pulses in one polarity and followed by a train of at least m number of pulses in the opposite polarity, where n and m are both equal to 2 or greater whole numbers. In some embodiments, n and m can be equal whole numbers and the sum of n pulses can be charge-balanced with the sum of m pulses. In some embodiments n pulses and m pulses can have a current amplitude or voltage amplitude which are different. Or, n and m can be unequal whole numbers and the sum of charges provided by n pulses can be charge-balanced with the sum of charges provided by m pulses.

In some embodiments, an implantable neurostimulator can comprise: an electrical circuit capable of delivering, through at least one electrode contact, a train of electrical stimuli that has at least n number of stimuli, where n is 3 or a greater whole number, such that each stimulus is represented by N1, N2, . . . , N-Last in one time window, and where the train of stimuli does not have a fixed frequency. As shown in FIG. 4D, the frequency may be variable as measured from the time duration between N1 and N2 compared to the time duration between N2 and N3. Or, the duration between adjacent stimuli can be entirely randomized with no fixed frequency, where the total number of stimuli N1, N2, . . . , N-Last occurring in a time window can be selected through software programming that is resident in the neurostimulator using the clinician programmer 802 or the patient programmer 801.

In some embodiments each stimuli N1, N2, . . . , N-Last can be biphasic, having both a peak in both polarity directions and also charge balanced. In some embodiments each stimuli N1, N2, . . . , N-Last can be symmetric and charge balanced. As shown in FIG. 4D, in some embodiments each stimuli N1, N2, . . . , N-Last can be biphasic and charged balanced, although not symmetric.

In a further embodiment, in accordance with the invention, a stimulation system is provided comprising: an implantable neurostimulator and at least one lead connected to the neurostimulator, the lead having one or more electrode contacts and configured to be implanted in the brain and where the neurostimulator is capable of providing a train of stimulation pulses having a frequency from about 20 Hz to about 50 KHz. The neurostimulator may be shaped and sized to be implanted subcutaneously in the head.

In yet a further embodiment, a deep brain stimulation (DBS) system can comprise: an implantable neurostimulator; and at least one stimulation lead that can be connected to the neurostimulator and the lead is implanted into the brain. The neurostimulator is capable of providing a selectable stimulus frequency in at least the range from about 100 Hz to about 4.8 KHz. In some embodiments, a neurostimulator can be capable of providing a selectable stimulus frequency in at least the range from about 500 Hz to about 4.8 kHz; in at least the range of about 100 Hz to about 4.8 kHz; and in at least the range of about 100 Hz to about 500 Hz. In the broadest range, the neurostimulator can have frequency range from about 20 Hz to about 50 kHz and that would provide the greatest stimulation options. However, this latter very wide frequency range may be technically difficult to implement and may be more expensive to build into a neurostimulator, so it may be advisable from a practical standpoint to use the suggested narrower ranges as mentioned, which will still provide a wide enough frequency range, compared to conventional spinal cord neurostimulators.

While the invention herein disclosed has been described by means of specific embodiments and applications thereof, numerous modifications and variations could be made thereto by those skilled in the art without departing from the scope of the invention set forth in the claims.

What is claimed is:

1. An implantable stimulation system comprising:
   a neurostimulator having a housing that is sized and shaped to be implanted in the head or neck;
   a patient programmer;
   a clinician programmer; and
   at least one stimulation lead that can be connected to the neurostimulator, the lead having one or more electrode contacts,
   wherein the neurostimulator is capable of providing a selectable stimulus frequency in at least the range from about 100 Hz to about 4.8 kHz.

2. The system of claim 1, wherein the neurostimulator is capable of providing a selectable stimulus frequency in at least the range from about 500 Hz to about 4.8 kHz.

3. The system of claim 1, wherein the neurostimulator is capable of providing a selectable stimulus frequency in at least the range from about 100 Hz to about 1 kHz.

4. The system of claim 1, wherein the neurostimulator is capable of providing a selectable stimulus frequency in at least the range from about 100 Hz to about 500 Hz.

5. The system of claim 1, wherein the at least one stimulation lead having one or more electrode contacts is configured to stimulate the occipital nerve or its branches.

6. The system of claim 1, wherein the at least one stimulation lead having one or more electrode contacts is configured to stimulate the trigeminal nerve or its branches.

7. The system of claim 1, wherein the at least one stimulation lead is a paddle-type lead, a cuff-type lead, or a linear-type lead, having one or more electrode contacts.

8. The system of claim 1, wherein the housing is not a return or indifferent electrode.

9. An implantable neurostimulator comprising:
   an electrical circuit capable of delivering a train of electrical stimuli that has at least a train of n number of pulses in one polarity and followed by a train of m number of pulses in the opposite polarity,
   wherein n and m are equal and are whole numbers greater than or equal to two, and wherein the sum of the train of n number of pulses is charge-balanced with the sum of the train of m number of pulses.

10. An implantable neurostimulator comprising:
an electrical circuit capable of delivering a train of electrical stimuli that has at least a train of n number of pulses in one polarity and followed by a train of m number of pulses in the opposite polarity,
wherein n and m are whole numbers of pulses greater than or equal to two, and
wherein the train of n number of pulses and the train of m number of pulses have a current amplitude or voltage amplitude which are substantially different.

11. An implantable neurostimulator comprising:
an electrical circuit capable of delivering a train of electrical stimuli that has at least a train of n number of pulses in one polarity and followed by a train of m number of pulses in the opposite polarity,
wherein n and m are unequal whole numbers greater than or equal to two, and
wherein the sum of charges provided by the train of n number of pulses is substantially charge-balanced with the sum of charges provided by the train of m number of pulses.

12. The neurostimulator of claim 10, wherein the neurostimulator is shaped and sized for implantation in the head or neck subcutaneously.

13. The neurostimulator of claim 10, wherein the neurostimulator is shaped and sized for implantation in the chest region or pectoral region of the body.

14. An implantable neurostimulator comprising:
an electrical circuit capable of delivering, through at least one electrode contact, a train of electrical stimuli that has at least n number of stimuli,
wherein n is 3 or a greater whole number, such that each stimulus is represented by N1, N2, . . . , N-Last in one time window, and
wherein the train of stimuli does not have a fixed frequency.

15. The neurostimulator of claim 14, wherein the frequency is not fixed but is variable as measured between the time duration between N1 and N2 compared to the time duration between N2 and N3.

16. The neurostimulator of claim 14, wherein the duration between adjacent stimuli is entirely randomized with no fixed frequency, wherein the total number of stimuli N1, N2, . . . , N-Last occurring in a time window can be selectable through software programming resident in the neurostimulator.

17. The neurostimulator of claim 14, wherein each stimuli N1, N2, . . . , N-Last is biphasic, having both a peak in both polarity directions and is charge balanced.

18. The neurostimulator of claim 17, wherein each stimuli NI, N2, . . . , N-Last is symmetric and charge balanced.

19. The neurostimulator of claim 17, wherein each stimuli N1, N2, . . . , N-Last is biphasic, not symmetric, and charge balanced.

20. The neurostimulator of claim 14, wherein the neurostimulator is sized and shaped to be implanted in the head or neck subcutaneously.

21. The neurostimulator of claim 14, wherein the housing is comprised of a conductive metal capable of being selected as an indifferent return electrode to operate in a monopolar stimulation mode.

22. A deep brain stimulation system comprising:
an implantable neurostimulator; and
at least one lead that can be connected to the neurostimulator, the lead having one or more electrode contacts and configured to be implanted in the brain,
wherein the neurostimulator is capable of providing a selectable stimulus frequency in at least the range from about 100 Hz to about 4.8 KHz.

23. The system of claim 22, wherein the neurostimulator is capable of providing a selectable stimulus frequency in at least the range from about 500 Hz to about 4.8 kHz.

24. The system of claim 22, wherein the neurostimulator is capable of providing a selectable stimulus frequency in at least the range from about 100 Hz to about 1 kHz.

25. The system of claim 22, wherein the neurostimulator is capable of providing a selectable stimulus frequency in at least the range from about 100 Hz to about 500 Hz.

* * * * *